United States Patent [19]

Hagiwara et al.

[11] Patent Number: 5,589,436
[45] Date of Patent: Dec. 31, 1996

[54] AGENT FOR PRESERVING THE FRESHNESS OF PLANTS

[75] Inventors: Hideaki Hagiwara, Takarazuka; Toshiaki Suzuki, Kasai, both of Japan

[73] Assignees: Yoshihide Hagiwara; HIH Biocenter, Inc., both of Takarazuka, Japan

[21] Appl. No.: 453,467

[22] Filed: May 30, 1995

[30] Foreign Application Priority Data

May 30, 1994 [JP] Japan .................................. 6-137855

[51] Int. Cl.$^6$ ..................................................... A01N 3/02
[52] U.S. Cl. ......................................................... 504/114
[58] Field of Search ............................................. 504/114

[56] References Cited

U.S. PATENT DOCUMENTS

| | | | |
|---|---|---|---|
| 5,112,380 | 5/1992 | Yamamoto et al. | 426/321 |
| 5,346,890 | 9/1994 | Hagiwara et al. | 514/27 |

FOREIGN PATENT DOCUMENTS

| | | |
|---|---|---|
| 0471584 | 1/1994 | European Pat. Off. . |
| 3624035 | 2/1987 | Germany . |
| 2312541 | 12/1990 | Japan . |
| 3204802 | 9/1991 | Japan . |
| 5124901 | 5/1993 | Japan . |
| 5124902 | 5/1993 | Japan . |
| 5139901 | 6/1993 | Japan . |

OTHER PUBLICATIONS

Database WPI, Section Ch, Week 7547, Derwent Publications Ltd., London, GB: Class E13, AN 75-77937W & JP-B-50 032 974 (JUJO Paper Mfg KK) Oct. 25, 1975.

Database WPI, Section Ch, Week 9122, Derwent Publications Ltd., London, GB Class E32, AN 91-159311 & JP-A-03 093 701 (Shinagawa Nenryo KK) Apr. 18, 1991.

Primary Examiner—S. Mark Clardy
Assistant Examiner—B. Bembenick
Attorney, Agent, or Firm—Sherman and Shalloway

[57] ABSTRACT

An agent for preserving the freshness of plants containing 2"-O-glucosylisovitexin as an effective ingredient is disclosed. This agent is excellent in an effect of preserving the freshness of cut flowers and potted plants, and, moreover, is safe and has no problem of the pollution of the environment.

10 Claims, No Drawings

AGENT FOR PRESERVING THE FRESHNESS OF PLANTS

This invention relates to an agent for preserving the freshness of plants, and relates particularly to a plant freshness-preserving agent particularly effective for preservation of the freshness of cut flowers.

As plant freshness-preserving agents, many ones containing silver ions, saccharides, germicides, surface active agents or the like have hitherto been used, but there are problems of safety, the pollution of the environment, etc. Therefore, various plant freshness-preserving agents having no such problems have recently been proposed (Japanese Laid-Open Patent Publication Nos. 312541/1990, 204802/1991, 124901/1993, 124902/1993, 139901/1993, etc.), but have drawbacks, e.g. of the freshness preservation effect being insufficient.

Thus, the present inventors had intensely researched into plant freshness-preserving agents which are excellent in plant freshness preservation effect, and are safe and have no problem of the pollution of the environment; as a result they now found that 2"-O-glucosylisovitexin represented by the following formula

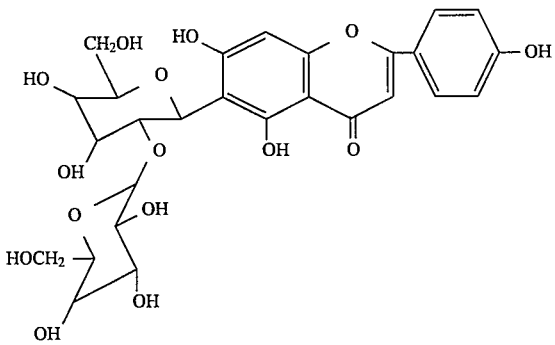

has an excellent freshness preservation effect on potted plants as well as cut flowers, and moreover, exhibits almost no toxicity on mammals and plants (phytotoxicity) and safe, and causes no pollution of the environment, and is thus extremely useful as a plant freshness-preserving agent; and completed this invention. Thus, this invention provides a plant freshness-preserving agent containing 2"-O-glucosylisovitexin as an effective ingredient.

The plant freshness-preserving agent of this invention is further detailedly described below.

2"-O-glucosylisovitexin as the effective ingredient of the plant freshness-preserving agent of this invention is a nature-derived substance excellent in antioxidant activity contained in various green plants, and can be obtained, for example according to the process described in U.S. Pat. No. 5,346,890 (EP-A-471584 and Japanese Laid-Open Patent Publication No. 65840/1993), for example by extracting the water insoluble components or n-hexane insoluble components of young leaves of barley with water-containing ethanol having a water content of 0 to 80 %, particularly preferably 15 to 50 %, if necessary extracting the components further with water-containing methanol having a water content of 0 to 80%, particularly preferably 30 to 60%, and if necessary subjecting the extract to operations such as chromatography and/or recrystallization.

It is not always necessary that 2"-O-glucosylisovitexin used in this invention is in a pure form, and it can be in the form of a crude extract.

The plant freshness-preserving agent of this invention can be in the form of powder or solution, but is usually preferably in the form of aqueous solution. The concentration of 2"-O-glucosylisovitexin in the aqueous solution not strictly limited, and can be varied depending on objects to be treated (cut flowers or potted plants or the like), application methods (spraying or immersion or the like), etc., but can generally be within the range of 0.001 ppm to 100 ppm. Suitably, in accordance with formulation forms, the concentration is preferably within the range of 0.01 ppm to 2 ppm in the case of spray agents, and an aqueous solution having such a concentration thereof can be made into products by filling it into spray vessels. The chemical can also be made into a thick solution within the range of 1 ppm to 10 ppm, and made into products by filling the solution into suitable vessels.

The plant freshness-preserving agent of this invention can, if desired, further contain surface active agens such as polyoxyethylenesorbitan monooleate and sorbitan monolaurate, various developers, organic solvents such as acetone and alcohols, and further, nutrients for plant, germicides, plant growth regulators, plant hormones, etc. can be incorporated in very small amounts.

The application method of the plant freshness-preserving agent of this invention varies depending on the kinds or forms of plants as objects to be treated, etc., but, in general, the application concentration of 2"-O-glucosylisovitexin in the case of aqueous solutions can be within the range of 0.00 1 ppm to 2 ppm, preferably 0.01 ppm to 1 ppm. Further, the way of treatment includes, for example, a method comprising spraying the plant freshness-preserving agent of this invention on part or the whole of plants such as cut flowers, sprays (cut sprays), leaves (cut leaves) and potted plants; a method comprising immersing the cut ends of plants such as cut flowers, sprays and leaves in a solution containing the plant freshness-preserving agent of this invention, or putting the solution in vases with such plants; a method comprises carrying out spray or immersion at the time of buds of flowers, etc.

Plants capable of being treated with the plant freshness-preserving agent of this invention include, for example, roses, carnations, chrysanthemums, marguerites, azaleas, dwarf azaleas, etc.

By using the plant freshness-preserving agent of this invention, such effects can be obtained, e.g., that it is possible to preserve long the flowering term of cut flowers, the flowering of the buds of cut flowers is accelerated, the freshness of leaves is preserved long, and it is possible to keep the flowers of potted plants fresh for a long time. Besides, as stated above, 2"-O-glucosylisovitexin as the effective ingredient of the plant freshness-preserving agent of this invention is derived from nature, and has various excellent advantages, e.g. that it is safe on animals and plants and has no problem of the pollution of the environment.

The effect of the plant freshness-preserving agent of this invention is further specifically described below according to test examples.

TEST EXAMPLE 1

2"-O-glucosylisovitexin (hereafter, abbreviated as GIV) having a purity of 80% extracted from young leaves of barley according to the method described in Example 1 of U.S. Pat. No. 5,346,890 (=Japanese Laid-Open Patent Publication No. 65480/1993) was diluted with water to give aqueous solutions having GIV concentrations of 0.1 ppm and 1 ppm, respectively.

Three vases each having a capacity of 800 ml were prepared, and 500 ml of the aqueous solution having a GIV concentration of 0.1 ppm was put in one of them (Sample A), and 500 ml portions of city water were put in the remaining two vases. Cut flowers (about 30 cm) of a rose untreated with chemicals, directly purchased from a farmer of rose cultivation, were put in the vases, respectively. About 1.5 ml of the aqueous solution having a GIV concentration of 1 ppm was sprayed once per every day on the rose in one of the vases containing city water (Sample B). The remaining one vase was used as a control.

Change of the state of the cut flowers of the rose was observed every day, and evaluation was conducted according to the following criterion.

○: blooming beautifully

Δ: the flower discolored

X : withered

The results are shown in the following Table 1.

TABLE 1

|  | Sample A | Sample B | Control |
| --- | --- | --- | --- |
| 3rd day | ○ | ○ | ○ |
| 5th day | ○ | ○ | ○ |
| 12th day | ○ | ○ | X |
| 16th day | ○ | ○ | X |
| 24th day | ○ | ○ | X |
| 31st day | Δ | X | X |
| 40th day | X | X | X |

TEST EXAMPLE 2

Three vases each having a capacity of 800 ml were prepared, and 800 ml of an aqueous solution having a GIV concentration of 0.01 ppm was put in one of them (Sample A), and 500 ml of an aqueous solution having a GIV concentration of 1 ppm was put in another one of them (Sample B), and 500 ml of city water was put in the remaining vase (control). Three each of cut flowers (about 30 cm) of a carnation, directly purchased from a cultivation farmer, were put in the vases, respectively, and change of the state of the cut flowers was evaluated based on the same criterion as in Test example 1. The results are shown in the following Table 2.

TABLE 2

|  | Sample A | Sample B | Control |
| --- | --- | --- | --- |
| 4rd day | ○○○ | ○○○ | ○○○ |
| 8th day | ○○○ | ○○○ | ○○○ |
| 12th day | ○○○ | ○○○ | ○○Δ |
| 16th day | ○○○ | ○○○ | ΔΔX |
| 20th day | ○○○ | ○○○ | XXX |
| 24st day | ○○Δ | ○ΔΔ | XXX |
| 28th day | XXX | XXX | XXX |

What is claimed is:

1. A method for preserving the freshness of cut flowers, cut sprays, cut leaves or a potted plant which comprises applying an effective amount of 2"-O-glucosylisovitexin thereto.

2. The method according to claim 1 which comprises applying an aqueous solution of the 2"-O-glucosylisovitexin.

3. The method according to claim 2 wherein the aqueous solution contains 2"-O-glucosylisovitexin in an amount of 0.001 ppm to 100 ppm.

4. The method according to claim 2 wherein the aqueous solution contains 2"-O-glucosylisovitexin in an amount of 0.01 to 2 ppm.

5. An aqueous composition for treating and preserving the freshness of plants comprising at least one of a plant nutrient, germicide, harmone or growth regulator, and 0.01 to 2 ppm of 2"-O-glucosylisovitexin.

6. The aqueous composition of claim 5 wherein the plant is cut flowers, cut sprays, cut leaves or a potted plant.

7. A method for preserving the freshness of cut flowers which comprises applying to the cut flowers an aqueous solution of an effective 0.01 to 2.0 ppm amount of 2"-O-glucosylisovitexin.

8. The method of claim 7 wherein the cut stems of the flowers are placed in the aqueous solution of the 2"-O-glucosylisovitexin.

9. The method of claim 7 wherein the cut flowers are sprayed with the aqueous solution of the 2"-O-glucosylisovitexin.

10. A method for preserving the freshness of a potted plant which comprises applying to the plant an aqueous solution of an effective 0.01 to 2.0 ppm amount of 2"-O-glucosylisovitexin.

* * * * *